United States Patent
Baloa Welzien et al.

(10) Patent No.: US 9,724,038 B2
(45) Date of Patent: Aug. 8, 2017

(54) SYSTEM AND METHOD FOR DETECTING SLEEP ONSET IN A SUBJECT BASED ON RESPONSIVENESS TO BREATHING CUES

(75) Inventors: Leonardo Alberto Baloa Welzien, Lake Forest, CA (US); Manuel Laura Lapoint, Pittsburgh, PA (US); Sara Marie Sibenaller, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 571 days.

(21) Appl. No.: 13/697,113

(22) PCT Filed: Apr. 25, 2011

(86) PCT No.: PCT/IB2011/051790
§ 371 (c)(1),
(2), (4) Date: Nov. 9, 2012

(87) PCT Pub. No.: WO2011/141843
PCT Pub. Date: Nov. 17, 2011

(65) Prior Publication Data
US 2013/0066226 A1    Mar. 14, 2013

Related U.S. Application Data

(60) Provisional application No. 61/334,597, filed on May 14, 2010.

(51) Int. Cl.
*A61B 5/08*    (2006.01)
*A61B 5/00*    (2006.01)
(Continued)

(52) U.S. Cl.
CPC .............. *A61B 5/4809* (2013.01); *A61B 5/03* (2013.01); *A61B 5/08* (2013.01); *A61B 5/087* (2013.01);
(Continued)

(58) Field of Classification Search
CPC ........... A61B 5/03; A61B 5/08; A61B 5/0816; A61B 5/082; A61B 5/0826; A61B 5/087;
(Continued)

(56) References Cited

U.S. PATENT DOCUMENTS

| 6,105,575 A | 8/2000 | Estes et al. |
| 6,731,984 B2 | 5/2004 | Cho et al. |

(Continued)

FOREIGN PATENT DOCUMENTS

| JP | 2009291307 A | 12/2009 |
| WO | 2009039525 A2 | 3/2009 |

OTHER PUBLICATIONS

Indu Ayappa et al; "Irregular Respiration as a Marker of Wakefulness Durig Titration of CPAP", Sleep, vol. 32, No. 1, 2009, pp. 99-104.
(Continued)

*Primary Examiner* — Jacqueline Cheng
*Assistant Examiner* — Puya Agahi

(57) ABSTRACT

A wake-to-sleep transition for a subject is detected based on responsiveness to breathing cues provided to the subject. A pressurized flow of breathable gas to the airway of subject having one or more gas parameters that are adjusted to provide breathing cues to the subject. Based on a detected conformance of the respiration of the subject to the breathing cues, a determination is made as to whether the subject is awake or asleep.

18 Claims, 3 Drawing Sheets

(51) Int. Cl.
*A61B 5/087* (2006.01)
*A61M 16/00* (2006.01)
*A61B 5/03* (2006.01)
*A61M 16/16* (2006.01)
*A61B 5/091* (2006.01)

(52) U.S. Cl.
CPC .......... *A61B 5/0816* (2013.01); *A61B 5/4806* (2013.01); *A61B 5/4812* (2013.01); *A61M 16/00* (2013.01); *A61M 16/0057* (2013.01); *A61M 16/161* (2014.02); *A61B 5/082* (2013.01); *A61B 5/0826* (2013.01); *A61B 5/091* (2013.01); *A61M 2016/003* (2013.01); *A61M 2016/0021* (2013.01); *A61M 2016/0027* (2013.01); *A61M 2016/0036* (2013.01); *A61M 2205/3331* (2013.01); *A61M 2205/3368* (2013.01); *A61M 2230/40* (2013.01); *A61M 2230/42* (2013.01); *A61M 2230/50* (2013.01)

(58) Field of Classification Search
CPC ..... A61B 5/091; A61B 5/4809; A61B 5/4806; A61B 5/4812; A61M 16/00; A61M 16/0057; A61M 16/161; A61M 2016/0021; A61M 2016/0027; A61M 2016/003; A61M 2016/0036; A61M 2205/3331; A61M 2205/3368; A61M 2230/40; A61M 2230/42; A61M 2230/50
See application file for complete search history.

(56) References Cited

U.S. PATENT DOCUMENTS

| 6,988,994 | B2 | 1/2006 | Rapoport et al. | |
|---|---|---|---|---|
| 7,186,221 | B2 | 3/2007 | Rapoport et al. | |
| 2006/0102179 | A1* | 5/2006 | Rapoport | A61B 5/0816 128/204.23 |
| 2006/0150974 | A1* | 7/2006 | Berthon-Jones | A61B 5/085 128/204.21 |
| 2007/0028920 | A1* | 2/2007 | Acker | A61M 16/0051 128/204.21 |
| 2007/0135725 | A1* | 6/2007 | Hatlestad | A61B 5/0809 600/529 |
| 2007/0208269 | A1 | 9/2007 | Mumford et al. | |
| 2008/0035147 | A1* | 2/2008 | Kirby | A61M 16/0051 128/204.21 |
| 2009/0299208 | A1 | 12/2009 | Takahashi et al. | |
| 2011/0297155 | A1* | 12/2011 | Shelly | A61M 16/00 128/204.23 |

OTHER PUBLICATIONS

Sven Rostig et al; "Nonrandom Variability of Respiration During Sleep in Healty Humans", Sleep Phuysiology, vol. 28, No. 4, 2005, pp. 411-417.

* cited by examiner

SYSTEM AND METHOD FOR DETECTING SLEEP ONSET IN A SUBJECT BASED ON RESPONSIVENESS TO BREATHING CUES

The invention relates to detection of sleep onset in a subject based on responsiveness to breathing cues provided to the subject.

DESCRIPTION OF THE RELATED ART

Devices configured to deliver positive airway pressure therapy to a subject are known. Typically, such devices are used to support the airway of the subject during sleep to reduce or eliminate obstructive respiratory events (e.g., apneas) during sleep. One of the drawbacks associated with known systems is that they tend to be uncomfortable before the subject falls asleep. While conventional systems provide mechanisms for reducing this discomfort, such as slowly ramping the pressure applied to the airway of the subject, they may consistently inhibit sleep in the subject if they do not delay therapy until after the onset of sleep.

One aspect of the invention relates to a system configured to detect an awake-to-sleep transition in a subject. In one embodiment, the system comprises a device, one or more sensors, and a processor. The device is configured to generate a pressurized flow of breathable gas for delivery to the airway of a subject. The one or more sensors are configured to generate output signals conveying information related to one or more gas parameters at or near the airway of the subject. The processor is configured to execute computer program modules, the computer program modules comprising a control module, a conformance module, and a sleep module. The control module is configured to control the device such that the device adjusts one or more parameters of the gas in the pressurized flow of breathable gas in order to provide breathing cues to the subject. The conformance module is configured to determine conformance of respiration of the subject to the breathing cues provided by the pressurized flow of breathable gas, such determination being based on the output signals generated by the one or more sensors and the cues provided by the pressurized flow of breathable gas. The sleep module is configured determine whether the subject is awake or asleep, such determination being based on the determination of conformance made by the conformance module.

Another aspect of the invention relates to a method of detecting an awake-to-sleep transition in a subject. In one embodiment, the method comprises generating a pressurized flow of breathable gas for delivery to the airway of a subject such that one or more parameters of the gas in the pressurized flow of breathable gas are adjusted in order to provide breathing cues to the subject; monitoring one or more breathing parameters of the respiration of the subject; determining conformance of respiration of the subject to the breathing cues provided by the pressurized flow of breathable gas, such determination being based on the monitored one or more breathing parameters and the cues provided by the pressurized flow of breathable gas; and determining whether the subject is awake or asleep, such determination being based on the determination of conformance.

Yet another aspect of the invention relates to a system configured to detect an awake-to-sleep transition in a subject. In one embodiment, the system comprises means for generating a pressurized flow of breathable gas for delivery to the airway of a subject such that one or more parameters of the gas in the pressurized flow of breathable gas are adjusted in order to provide breathing cues to the subject; means for monitoring one or more breathing parameters of the respiration of the subject; means for determining conformance of respiration of the subject to the breathing cues provided by the pressurized flow of breathable gas, such determination being based on the monitored one or more breathing parameters and the cues provided by the pressurized flow of breathable gas; and means for determining whether the subject is awake or asleep, such determination being based on the determination of conformance.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
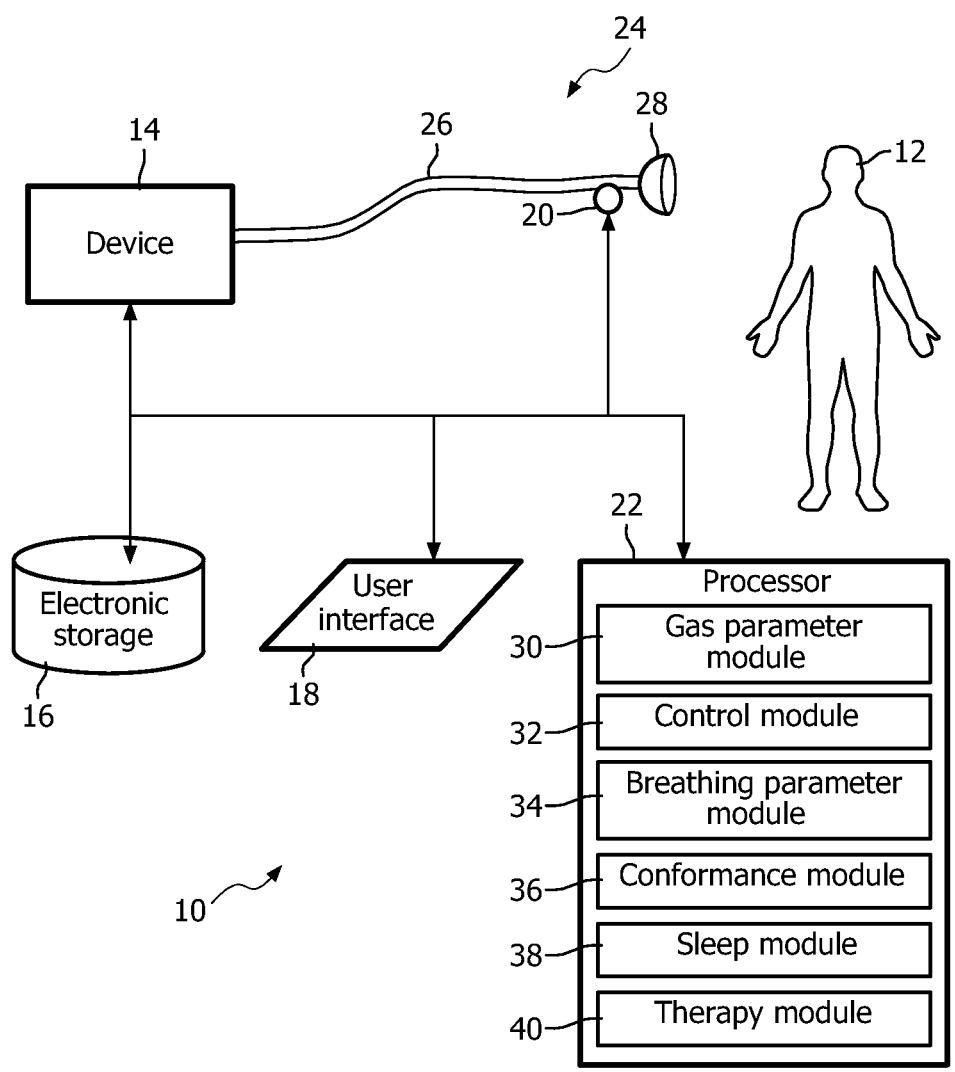
FIG. 1 illustrates a system configured to detect a wake-to-sleep transition for a subject, according to one or more embodiments of the invention.

FIG. 1 illustrates a system 10 configured to detect a wake-to-sleep transition for a subject 12. The system 10 provides pressurized flow of breathable gas to the airway of subject 12, and adjusts one or more gas parameters of the gas in the pressurized flow of breathable gas to provide breathing cues to subject 12 that encourage subject 12 to consciously adjust respiration such that the one or more breathing parameters are altered. Based on a detected conformance of the respiration of subject 12 to the breathing cues, a determination is made as to whether subject 12 is awake or asleep. In one embodiment, system 10 may include a pressure generator 14, electronic storage 16, a user interface 18, one or more sensors 20, a processor 22, and/or other components.

In one embodiment, pressure generator 14 includes a positive pressure support device. A positive pressure support device is well-known and is disclosed, for example, in U.S. Pat. No. 6,105,575, hereby incorporated by reference in its entirety. In this embodiment, pressure generator 14 is configured to deliver a pressurized flow of breathable gas to the airway of subject 12.

Pressure generator 14 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode for generating the pressurized flow of breathable gas is Inspiratory Positive Air Pressure (IPAP). One example of the IPAP mode is bi-level positive air pressure (BiPAP). In BiPAP, two levels of positive air pressure (HI and LO) are supplied to a subject. Other modes of generating the pressurized flow of breathable gas are contemplated.

Generally, the timing of the HI and LO levels of pressure are controlled such that the HI level of positive air pressure is delivered to subject 12 during inhalation and the LO level of pressure is delivered to subject 12 during exhalation. In conventional positive pressure support devices, the timing of the HI and LO levels of pressure is coordinated to coincide with the breathing of subject 12 based on detection of gas parameters that indicate whether a user is currently inhaling or exhaling.

The pressurized flow of breathable gas is delivered to the airway of subject 12 via a subject interface 24. Subject interface 24 is configured to communicate the pressurized flow of breathable gas generated by device 14 to the airway of subject 12. As such, subject interface 24 includes a conduit 26 and an interface appliance 28. Conduit conveys the pressurized flow of breathable gas to interface appliance 28, and interface appliance 28 delivers the pressurized flow of breathable gas to the airway of subject 12. Some examples of interface appliance 28 may include, for example, an endotracheal tube, a nasal cannula, a tracheotomy tube, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronically storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., device 14, user interface 18, processor 22, etc.).

User interface 18 is configured to provide an interface between system 10 and subject 12 through which subject 12 may provide information to and receive information from system 10. This enables data, results, and/or instructions and any other communicable items, collectively referred to as "information," to be communicated between the subject 12 and one or more of device 14, electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, and/or other interface devices. In one embodiment, user interface 18 includes a plurality of separate interfaces. In one embodiment, user interface 18 includes at least one interface that is provided integrally with device 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

One or more sensors 20 are configured to generate one or more output signals conveying information related to one or more gas parameters of the gas breathed by subject 12. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. In an embodiment in which a pressurized flow of breathable gas is delivered to subject 12 from device 14, sensors 20 include sensors in communication with gas within subject interface 24.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device, or processor 22 may represent processing functionality of a plurality of devices operating in coordination.

As is shown in FIG. 1, processor 22 may be configured to execute one or more computer program modules. The one or more computer program modules may include one or more of a gas parameter module 30, a control module 32, a breathing parameter module 34, a conformance module 36, a sleep module 38, a therapy module 40, and/or other modules. Processor 22 may be configured to execute modules 30, 32, 34, 36, 38, and/or 40 by software; hardware; firmware; some combination of software, hardware, and/or firmware; and/or other mechanisms for configuring processing capabilities on processor 22.

It should be appreciated that although modules 30, 32, 34, 36, 38, and/or 40 are illustrated in FIG. 1 as being co-located within a single processing unit, in implementations in which processor 22 includes multiple processing units, one or more of modules 30, 32, 34, 36, 38, and/or 40 may be located remotely from the other modules. The description of the functionality provided by the different modules 30, 32, 34, 36, 38, and/or 40 described below is for illustrative purposes, and is not intended to be limiting, as any of modules 30, 32, 34, 36, 38, and/or 40 may provide more or less functionality than is described. For example, one or more of modules 30, 32, 34, 36, 38, and/or 40 may be eliminated, and some or all of its functionality may be provided by other ones of modules 30, 32, 34, 36, 38, and/or 40. As another example, processor 22 may be configured to execute one or more additional modules that may perform some or all of the functionality attributed below to one of modules 30, 32, 34, 36, 38, and/or 40.

The gas parameter module 30 is configured to determine information related to one or more gas parameters of the pressurized flow of breathable gas that is generated by device 14 and delivered to the airway of subject 12 via subject interface 24. The one or more gas parameters are determined based on the output signals of sensors 20. The one or more gas parameters may include one or more of a pressure, a flow rate, a peak flow, a composition, a humidity, a temperature, an acceleration, a velocity, a thermal energy dissipated (e.g., in a mass flowmeter, etc.), and/or other gas parameters.

Control module 36 is configured to control device 14. Controlling device 14 includes adjusting the breathing cues provided to subject 12 by device 14. As was mentioned above, in one embodiment, the breathing cues administered to subject 12 by device 14 include changes to one or more parameters of the pressurized flow of breathable gas delivered from device 14 to subject 12. For example, the one or more parameters may include a pressure, a flow rate, and/or a volume of the pressurized flow of breathable gas. Control module 36 adjusts the breathing cues provided to subject 12 be device 14 in order to prompt subject 12 to bring the one or more breathing parameters into conformance with the target.

For example, in an embodiment in which device 14 generates the pressurized flow of breathable gas according to a BiPAP mode, control module 36 may control device 14 to adjust the pressure, flow rate, and/or volume of gas delivered to the airway of subject 12 while the pressurized flow of breathable gas is being generated at the HI pressure (e.g, during inhalation). Adjusting the pressure, flow rate, and/or volume of gas delivered to the airway of subject 12 while the pressurized flow of breathable gas is being generated at the HI pressure will tend to generate breathing cues that prompt subject 12 to begin inspiration, alter the volume of gas inhaled, to alter the inspiration period, to alter the inspiration flow rate, to alter the tidal volume, and/or to otherwise consciously alter one or more other breathing parameters.

As another example, in an embodiment in which device 14 generates the pressurized flow of breathable gas according to a BiPAP mode, control module 36 may control device 14 to adjust the pressure flow rate, and/or volume of gas delivered to the airway of subject 12 while the pressurized flow of breathable gas is being generated at the LO pressure (e.g., during exhalation). Adjusting the pressure, flow rate, and/or volume of gas delivered to the airway of subject 12 while the pressurized flow of breathable gas is being generated at the LO pressure may result in breathing cues that tend to prompt subject 12 to begin exhalation, to adjust the exhalation period, the exhalation flow rate, the peak flow of respiration, the tidal volume, and/or to otherwise consciously alter one or more other breathing parameters.

As yet another example, in an embodiment in which device 14 generates the pressurized flow of breathable gas according to a BiPAP mode, control module 36 may control device 14 to adjust a period of the HI and/or LO pressure cycles, a pressure curve shape during a transition between HI and LO pressure cycles, a flow rate curve shape during a transition between HI and LO pressure cycles, and/or adjust other gas parameters of the pressurized flow of breathable gas. As will be appreciated, such adjustments to the gas parameters of the pressurized flow of breathable gas will tend to provide breathing cues to subject 12 to consciously alter one or more breathing parameters. For example, such breathing cues may prompt subject 12 to alter one or more of a breathing rate, a breath period, a respiration flow curve shape, a respiration pressure curve shape, a timing of an inspiration-to-expiration transition, a timing of an expiration-to-inspiration transition, and/or other breathing parameters.

The breathing parameter module 34 is configured to determine one or more breathing parameters of the respiration of subject 12. The breathing parameter module 32 may determine the one or more breathing parameters based on the one or more gas parameters determined by gas parameter module 30 and/or from the output signals generated by sensors 20. The one or more breathing parameters include the one or more breathing parameters that subject 12 is prompted to consciously alter by the breathing cues provided in the pressurized flow of breathable gas. For example, the one or more breathing parameters may include one or more of an inhalation flow rate, an inhalation period, an exhalation flow rate, an exhalation period, a tidal volume, a breathing rate, a breath period, a peak flow, a flow curve shape, a pressure curve shape, expiration-to-inspiration transitions, inspiration-to-expiration transitions, and/or other breathing parameters.

The conformance module 36 is configured to determine conformance of respiration of subject 12 with the breathing cues provided by the pressurized flow of breathable gas. The determination of conformance made by conformance module 36 is based on the output signals generated by sensors 20 and the cues provided by the pressurized flow of breathable gas. In one embodiment, conformance module 36 compares one or more of the breathing parameters determined by breathing parameter module 34 (which are determined based on the output signals of sensors 20) to the cues.

Determining conformance of respiration of subject 12 with the breathing cues includes determining a metric that quantifies the conformance, or synchronicity, of the respiration of subject 12 with the breathing cues. For example, a breath rate of subject 12, or a difference between breath rate of subject 12 and the breath rate prompted by the breathing cues may indicate conformance of the respiration of subject 12.

The metric may quantify the conformance on a per-breath basis. By way of non-limiting example, conformance of the respiration of subject 12 may be quantified by a difference between an amount of time breathing cues provided by the pressurized flow of breathable gas prompt subject 12 to inhale, and an actual amount of time subject 12 inhales. Hereafter, this difference is referred to "inspiration extension time". Similarly, another non-limiting example of a metric that quantifies conformance of the respiration of subject 12 is a different between an amount of time breathing cues provided by the pressurized flow of breathable gas prompt subject 12 to exhale, and an actual amount of time subject 12 exhales. This difference is referred to as "expiration extension time."

If the metric quantifies conformance of the respiration of subject 12 to the breathing cues on a per-breath basis, determining conformance of subject 12 may include determining a per-breath average of the metric for a plurality of breaths. This may reduce noise caused for individual breaths by breathing irregularity, momentary inattentiveness, and/or other phenomena. The number of breaths used to determine the average may be a user-configurable setting or may be a set value. In one embodiment, conformance module 36 is configured to determine the number of breaths used to determine the average through observation of subject 12 over time. For example, at a first number of breaths, the average may be found to be too noisy (e.g., giving rise to false detections of sleepfulness), while at a second number of breaths the average may be found to not be sensitive enough (e.g., giving rise to belated detections of sleepfulness). The conformance module 36 may be configured to observe such results, and to identify a third number of breaths between the first number and the second number as an appropriate number of breaths to implement in determining the average of the metric for subject 12.

Figure 2:
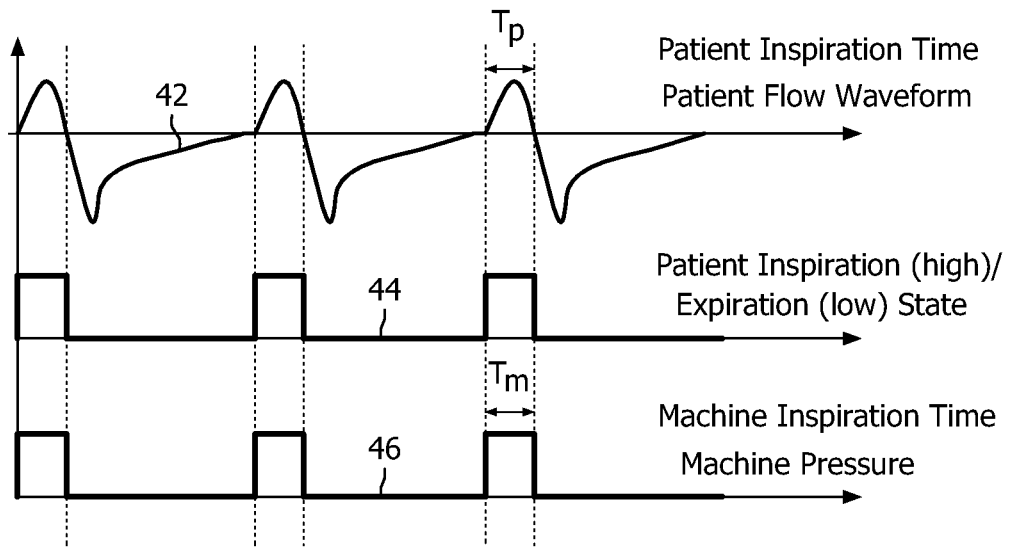
FIG. 2 illustrates a plot of flow at or near the airway of a subject, a plot of inspiration/expiration state for the subject, and a plot of pressure of a pressurized flow of breathable gas delivered to the airway of the subject to provide breathing cues to the subject.

FIG. 2 illustrates a plot 42 of flow at or near the airway of a subject, a plot 44 of the inspiration/expiration state for the subject, and a plot 46 of pressure of a pressurized flow of breathable gas delivered to the airway of the subject to provide breathing cues to the subject. Specifically, in FIG. 2, the subject is awake and is exhibiting respiration that conforms to the breathing cues. As such, the transitions in breathing between exhale and inhale, and between inhale and exhale for the subject coincide with changes in the pressure of the pressurized flow of breathable gas. For example, the inspiration extension time and/or the expiration extension time for plots 44 and 46 would be zero, or de minimis.

Figure 3:
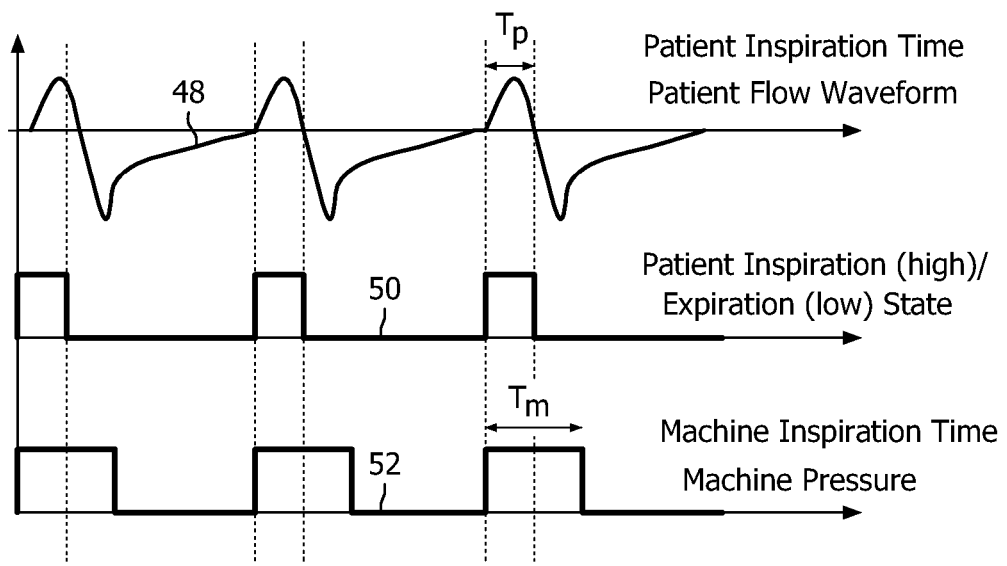
FIG. 3 illustrates a plot of flow at or near the airway of a subject, a plot of inspiration/expiration state for the subject, and a plot of pressure of a pressurized flow of breathable gas delivered to the airway of the subject to provide breathing cues to the subject.

FIG. 3 illustrates a plot 48 of flow at or near the airway of a subject, a plot 50 of inspiration/expiration state for the subject, and a plot 52 of pressure of a pressurized flow of breathable gas delivered to the airway of the subject to provide breathing cues. In plots 48, 50, and 52, the subject is asleep, and is therefore not following the breathing cues provided by the pressurized flow of breathable gas. For example, the inspirations of the subject are not extending to the full period of the breathing cues. As such, the inspiration extension time for these breaths will be substantially longer than the inspiration extension time for the breaths depicted in FIG. 2.

Returning to FIG. 1, sleep module 38 is configured to determine whether subject 12 is awake or asleep. The determination is based on the determination of conformance by conformance module 36. For example, in one embodiment, sleep module 38 compares the metric quantifying conformance that was determined by conformance module 36 with a threshold level of conformance. If the metric quantifying conformance does not breach the threshold level, then sleep module 38 determines that subject 12 is still awake and breathing in conformance with the cues provided by the pressurized flow of breathable gas. If the metric quantifying conformance breaches the threshold level, then sleep module 38 determines that subject 12 is asleep, thereby causing the breathing of subject 12 to no longer conform to the cues provided by the pressurized flow of breathable gas. The threshold may be a static value or level. The static value or level may be determined based on user-selection, and/or permanent (or semi-permanent) setting. The threshold may be a dynamic value or level. For example, sleep module 38 may determine the appropriate threshold of subject 12 individually over time. The sleep module 38 may accomplish this by tuning the value or level used as the threshold to minimize both false detections of sleep and delayed detections of sleep.

In one embodiment, control module 32 is configured such that the breathing cues provided to subject 12 by the pressurized flow of breathable gas remain constant during a therapy session. In one embodiment, control module 32 is configured such that the breathing cues provided to subject 12 by pressurized flow of breathable gas change slowly throughout the session. For example, the breathing cues may change during the session to slowly change breathing rate, inspiration time, expiration time, and/or other breathing parameters. These gradual changes in the breathing cues may facilitate detection of sleep, as a lack of synchronization between the respiration of subject 12 and the breathing cues may be easier to detect if the breathing cues are dynamic.

By way of non-limiting example, the inspiration time of the breathing cues may slowly expand during the therapy session. This will tend to relax subject 12, but will also highlight the point in time when subject 12 is no longer following the breathing cues due to the onset of sleep. This is because once subject 12 goes to sleep the inspiration time of the breathing of subject 12 will return to its natural state.

Figure 4:
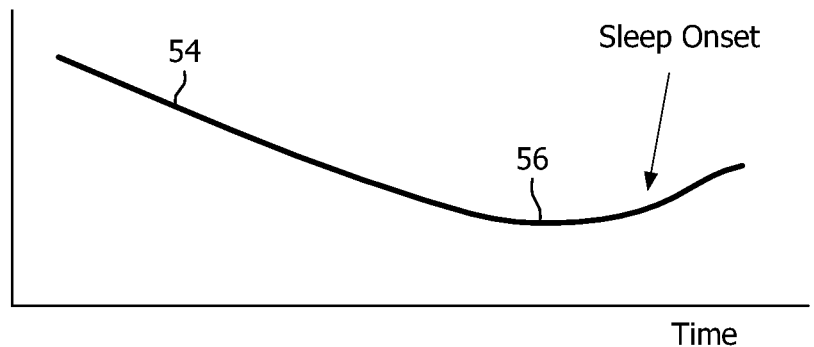
FIG. 4 illustrates a plot of breath rate as a subject receives therapy from a system configured to detect a wake-to-sleep transition for a subject, according to one or more embodiments of the invention.

As another non-limiting example, FIG. 4 illustrates a plot 54 of breath rate as a subject receives therapy from a system similar to or the same as system 10 (shown in FIG. 1 and described above). The plot 54 illustrates how the breathing cues provided to the subject can slowly reduce the breath rate of the subject over time, and how once the subject goes to sleep, a local minima 56 is formed in breath rate because the breath rate begins to climb back to its natural value.

Referring back to FIG. 1, it will be appreciated that sleep module 38 may be configured to base the determination of whether subject 12 is awake or asleep on more than a single metric of conformance determined by conformance module 36. Further, in one embodiment, sleep module 38 further supplements the determination of whether subject 12 is awake or asleep on other analysis of breathing parameters determined by breathing parameter module 34 that can be indicative of sleepfulness. By way of non-limiting example, such breathing parameters may include one or more of breath to breath variability of a breathing parameter (e.g., volume, duration, inspiration percentage, expiration percentage, minute ventilation, breath rate, etc.), intrabreath variability in one or more breathing parameters, drops in one or more breathing parameters, dynamic frequency interbreath variability, and/or other analysis of breathing parameters.

The therapy module 40 is configured to control pressure generator 14 to administer a pressure support therapy to subject 12 while subject 12 sleeps. The administration of the pressure support therapy is triggered by a determination by sleep module 38 that subject 12 is asleep. Responsive to a determination by sleep module 38 that subject 12 is asleep, therapy module 40 is configured to begin the pressure support therapy. Commencing the pressure support therapy may include ramping up pressure at or near the airway of subject 12 to support the airway of subject 12 during sleep to reduce obstructive respiratory events. The pressure support therapy may include, for example, one or more of BiPAP®, continuous positive airway pressure therapy, and/or other forms of positive airway pressure therapy.

Figure 5:
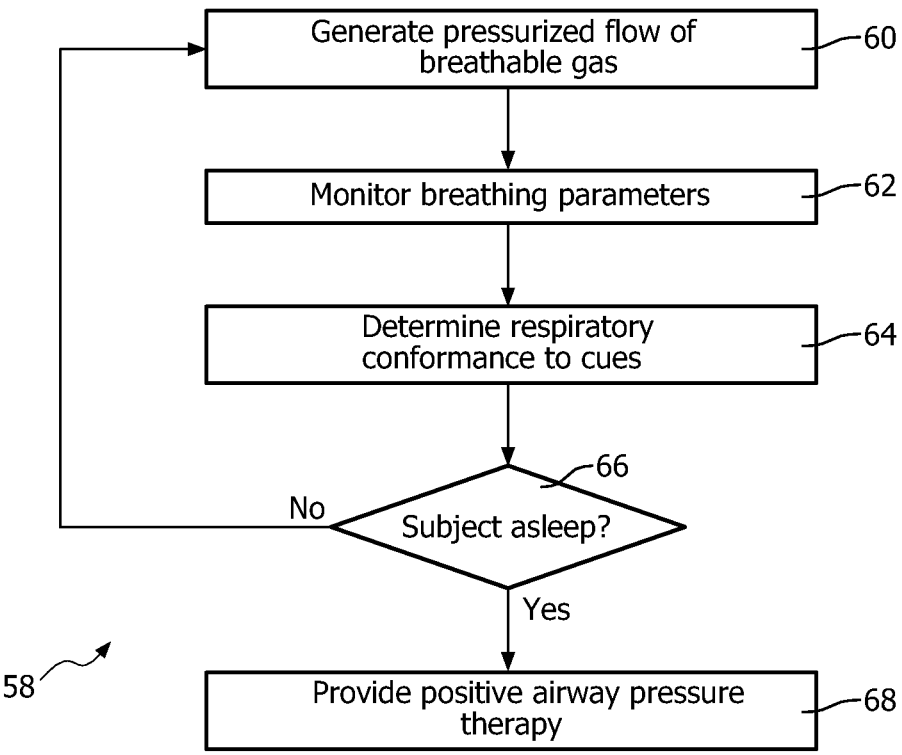
FIG. 5 illustrates a method of detecting an awake-to-asleep transition in a subject, according to one or more embodiments of the invention.

FIG. 5 illustrates a method 58 of detecting an awake-to-asleep transition in a subject. The operations of method 58 presented below are intended to be illustrative. In some embodiments, method 58 may be accomplished with one or more additional operations not described, and/or without one or more of the operations discussed. Additionally, the order in which the operations of method 58 are illustrated in FIG. 5 and described below is not intended to be limiting.

In some embodiments, method 58 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 58 in response to instructions stored electronically on an electronic storage medium. The one or more processing devices may include one or more devices configured through hardware, firmware, and/or software to be specifically designed for execution of one or more of the operations of method 58.

At an operation 60, a pressurized flow of breathable gas is generated for delivery to the airway of a subject. The pressurized flow of breathable gas is generated such that one or more parameters of the gas in the pressurized flow of breathable gas are adjusted in order to provide breathing cues to the subject. The breathing cues prompt the subject to alter one or more breathing parameters. In one embodiment, operation 60 is performed by a device similar to or the same as device 14 (shown in FIG. 1 and described above) under control of a control module similar to or the same as control module 32 (shown in FIG. 1 and described above).

At an operation 62, one or more breathing parameters of the respiration of the subject are monitored. Monitoring the one or more breathing parameters may include determining the one or more breathing parameters. The one or more breathing parameters may be determined based on output signals generated by sensors conveying information related to gas parameters at or near the airway of the subject. In one embodiment, operation 62 may be performed by a breathing parameter module similar to or the same as breathing parameter module 34 (shown in FIG. 1 and described above).

At an operation 64, conformance of respiration of the subject to the breathing cues provided at operation 60 is determined. Determining the conformance of the respiration of the subject to the breathing cues may include determining a metric that quantifies respiratory conformance. In one embodiment, the metric quantifies conformance on a per-breath basis. In this embodiment, determining respiratory conformance may include determining an average of the metric over a plurality of breaths (e.g., consecutive breaths, breaths that are proximate in time, etc.). The conformance of the respiration of the subject to the breathing cues may be determined based on the monitored one or more breathing parameters and/or breathing cues. In one embodiment, operation 64 is performed by a conformance module similar to or the same as conformance module 36 (shown in FIG. 1 and described above).

At an operation 66, a determination is made as to whether the subject is asleep or awake. This determination may include comparing the conformance of the respiration of the subject with the breathing cues (determined at operation 64) with a threshold level of conformance. If the conformance of the respiration of the subject does not breach a threshold level, it is determined that the subject is still awake. If the conformance of the respiration of the subject breaches the threshold level, it is determined that the subject is asleep. The determination as to whether the subject is asleep or awake may further be supplemented by other analysis of the breathing parameters determined at operation 64. In one embodiment, operation 66 is performed by a sleep module similar to or the same as sleep module 38 (shown in FIG. 1 and described above).

If the determination is made at operation 66 that the subject is awake, method 58 continues to iterate through operations 60, 62, 64, and back to operation 66. If the determination is made at operation 66 that the subject is asleep, method 58 proceeds to an operation 68. At operation 68, a respiratory therapy is provided to the subject by the pressurized flow of breathable gas. For example, the respiratory therapy may include a positive airway pressure therapy. In one embodiment, operation 68 is performed by a therapy module similar to or the same as therapy module 40 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to provide sleep-triggered pressure-based airway support therapy for a subject via pressure-based breathing cues and breathing-cue based sleep detection, the system comprising:
   one or more pressure generators configured to generate a pressurized flow of breathable gas for delivery to the airway of the subject;
   one or more sensors for placement at or near an airway of the subject to obtain and measure gas at or near the airway of the subject and configured to generate output sensor signals conveying information related to a gas parameter of the pressurized flow of breathable gas at or near the airway of the subject; and
   one or more physical computer processors configured by computer readable instructions to:
   cause, via at least one of the one or more pressure generators, multiple adjustments of the pressurized flow of breathable gas over a period of time to provide breathing cues to the subject;
   determine conformance of respiration of the subject to the breathing cues provided by the multiple adjustments of the pressurized flow of breathable gas, the conformation determination being based on the output sensor signals and the breathing cues, the conformance determination comprising determining a conformance metric that quantifies a synchronization difference between respiration of the subject and the breathing cues for a predetermined number of breaths, wherein the predetermined number of breaths is greater than one and adjusted based on a noise level in the conformance metric for the predetermined number of breaths;
   determine a threshold level of conformance for the subject over a period of time;
   detect that the subject is asleep based on the conformance metric breaching the threshold level of conformance; and
   responsive to detecting that the subject is asleep, initiate a pressure support therapy to support the airway of the subject using at least one of the one or more pressure generators to increase pressure at or near the airway of the subject.

2. The system of claim 1, wherein the detection that the subject is asleep is based on analysis of one or more of a breath to breath variability of one or more breathing parameters, an intrabreath variability in the one or more breathing parameters, a drop in the one or more breathing parameters, or a dynamic frequency interbreath variability.

3. The system of claim 1, wherein the one or more physical computer processors are further configured such that the conformance metric quantifies conformance on an individual breath basis for the predetermined number of breaths.

4. The system of claim 3, wherein the one or more physical computer processors are further configured such that the conformance metric comprises an average inspiration extension time or an average expiration extension time over the predetermined number of breaths.

5. The system of claim 1, wherein the one or more physical computer processors cause the multiple adjustments of the pressurized flow of breathable gas by causing, via at least one of the one ore more pressure generators, multiple pressure adjustments or flow rate adjustments to the pressurized flow of breathable gas over a period of time to provide breathing cues to the subject.

6. A method of detecting an awake-to-sleep transition in a subject, the method comprising:
generating, with one or more pressure generators, a pressurized flow of breathable gas for delivery to the airway of the subject;
obtaining, with one or more sensors placed at or near the airway of the subject, output sensor signals conveying information related to a gas parameter of the pressurized flow of breathable gas;
causing, with one or more processors, via a pressure generator, multiple adjustments of the pressurized flow of breathable gas over a period of time to provide breathing cues to the subject;
determining, with one or more processors, conformance of respiration of the subject to the breathings cues provided by the multiple adjustments of the pressurized flow of breathable gas, the conformance determination being based on the output sensor signals and the breathing cues, the conformance determination comprising determining a conformance metric that quantifies a synchronization difference between respiration of the subject and the breathing cues for a predetermined number of breaths, wherein the predetermined number of breaths is greater than one and adjusted based on a noise level in the conformance metric for the predetermined number of breaths;
determining, with the one or more processors, a threshold level of conformance for the subject over a period of time;
detecting, with the one or more processors, that the subject is asleep based on the conformance metric breaching the threshold level of conformance; and
responsive to detecting that the subject is asleep, initiating, with the one or more processors, a pressure support therapy to support the airway of the subject using at least one of the one or more pressure generators to increase pressure at or near the airway of the subject.

7. The method of claim 6, wherein the conformance metric quantifies conformance on an individual breath basis for the predetermined number of breaths.

8. The method of claim 6, wherein causing the multiple adjustments of the pressurized flow of breathable gas comprises causing, via a pressure generator, multiple pressure adjustments or flow rate adjustments to the pressurized flow of breathable gas over a period of time to provide breathing cues to the subject.

9. A system configured to detect an awake-to-sleep transition in a subject, the system comprising:
means for obtaining sensor information related to a gas parameter of the pressurized flow of breathable gas;
means for causing multiple adjustments of the pressurized flow of breathable gas over a period of time to provide breathing cues to the subject;
means for determining conformance of respiration of the subject to the breathing cues provided by the multiple adjustments of the pressurized flow of breathable gas, the conformance determination being based on the output sensor signals and the breathing cues, the conformance determination comprising determining a conformance metric that quantifies a synchronization difference between respiration of the subject and the breathing cues for a predetermined number of breaths, wherein the predetermined number of breaths is greater than one and adjusted based on a noise level in the conformance metric for the predetermined number of breaths;
means for determining a threshold level of conformance for the subject over a period of time;
means for detecting that the subject is asleep based on the conformance metric breaching the threshold level of conformance; and
means for, responsive to detecting that the subject is asleep, initiating a pressure support therapy to support the airway of the subject to increase pressure at or near the airway of the subject.

10. The system of claim 9, wherein the conformance metric quantifies conformance on an individual breath basis for the predetermined number of breaths.

11. The system of claim 9, wherein causing the multiple adjustments of the pressurized flow of breathable gas comprises causing multiple pressure adjustments or flow rate adjustments to the pressurized flow of breathable gas over a period of time to provide breathing cues to the subject.

12. The system of claim 1, wherein the breathing cues gradually change from breath to breath.

13. The system of claim 12, wherein the gradually changing breathing cues comprises a gradual change in one or more of a breathing rate, inspiration time, expiration time, exhalation flow rate, peak flow of respiration, or tidal volume from breath to breath.

14. The method of claim 6, wherein the breathing cues gradually change from breath to breath.

15. The method of claim 14, wherein the gradually changing breathing cues comprises a gradual change in one or more of a breathing rate, inspiration time, expiration time, exhalation flow rate, peak flow of respiration, or tidal volume from breath to breath.

16. The system of claim 9, wherein the breathing cues gradually change from breath to breath, and wherein the gradually changing breathing cues comprises a gradual change in one or more of a breathing rate, inspiration time, expiration time, exhalation flow rate, peak flow of respiration, or tidal volume from breath to breath.

17. The system of claim 1, wherein the one or more physical computer processors are further configured to:
determine the noise level in the conformance metric; and adjust the predetermined number of breaths to be measured,
wherein determining the conformance metric comprises determining the conformance metric based on the adjusted predetermined number of breadths.

18. The system of claim 1, wherein the one or more physical computer processors are further configured to:
iteratively perform over a period of time, until at least detection that the subject is asleep, the following:
(1) the multiple adjustments of the pressurized flow of breathable gas;
(2) the determination of conformance of respiration of the subject to the breathing cues, including the determination of the conformance metric; and
(3) the determination of the threshold level of conformance.

* * * * *